US007877140B2

(12) United States Patent
Stahmann et al.

(10) Patent No.: US 7,877,140 B2
(45) Date of Patent: *Jan. 25, 2011

(54) PRESSURE SENSING FOR FEEDBACK CONTROL OF POST-MI REMODELING CONTROL PACING

(75) Inventors: Jeffrey E. Stahmann, Ramsey, MN (US); Joseph M. Pastore, Woodbury, MN (US); Andrew P. Kramer, Stillwater, MN (US); Rodney W. Salo, Fridley, MN (US); Jesse W. Hartley, Lino Lakes, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 351 days.

This patent is subject to a terminal disclaimer.

(21) Appl. No.: 11/220,023

(22) Filed: Sep. 6, 2005

(65) Prior Publication Data

US 2007/0055317 A1  Mar. 8, 2007

(51) Int. Cl.
*A61N 1/368* (2006.01)
(52) U.S. Cl. ............................................. 607/9; 607/17
(58) Field of Classification Search .................. 607/9, 607/17–19, 23, 24, 123
See application file for complete search history.

(56) References Cited

U.S. PATENT DOCUMENTS

| 5,052,388 | A | * | 10/1991 | Sivula et al. ................. 607/22 |
| 5,190,035 | A | | 3/1993 | Salo et al. |
| 6,161,042 | A | | 12/2000 | Hartley et al. |
| 6,450,942 | B1 | * | 9/2002 | Lapanashvili et al. ......... 600/16 |
| 6,542,775 | B2 | * | 4/2003 | Ding et al. .................... 607/24 |
| 6,628,988 | B2 | * | 9/2003 | Kramer et al. ................ 607/9 |
| 2003/0105493 | A1 | * | 6/2003 | Salo ............................. 607/9 |
| 2003/0114889 | A1 | * | 6/2003 | Huvelle et al. ............... 607/17 |
| 2004/0049235 | A1 | * | 3/2004 | Deno et al. ................... 607/9 |
| 2004/0049236 | A1 | * | 3/2004 | Kramer et al. ................ 607/9 |
| 2005/0065554 | A1 | * | 3/2005 | KenKnight et al. ........... 607/4 |
| 2005/0137632 | A1 | * | 6/2005 | Ding et al. .................... 607/9 |
| 2006/0287683 | A1 | | 12/2006 | Pastore et al. |

* cited by examiner

*Primary Examiner*—Carl H Layno
*Assistant Examiner*—Gary A Porter, Jr.
(74) *Attorney, Agent, or Firm*—Schwegman, Lundberg & Woessner, P.A.

(57) ABSTRACT

A method and device for delivering pre-excitation pacing to prevent or reduce cardiac remodeling following a myocardial infarction is described. The pre-excitation pacing is modulated in accordance with an intravascular pressure measurement in order to balance the beneficial effects of stress reduction with hemodynamic compromise.

18 Claims, 4 Drawing Sheets

PRESSURE SENSING FOR FEEDBACK CONTROL OF POST-MI REMODELING CONTROL PACING

FIELD OF THE INVENTION

This patent application pertains to methods and apparatus for the treatment of cardiac disease. In particular, it relates to methods and apparatus for improving cardiac function with electro-stimulatory therapy.

BACKGROUND

A myocardial infarction (MI) is the irreversible damage done to a segment of heart muscle by ischemia, where the myocardium is deprived of adequate oxygen and metabolite removal due to an interruption in blood supply. It is usually due to a sudden thrombotic occlusion of a coronary artery, commonly called a heart attack. If the coronary artery becomes completely occluded and there is poor collateral blood flow to the affected area, a transmural or full-wall thickness infarct can result in which much of the contractile function of the area is lost. Over a period of one to two months, the necrotic tissue heals, leaving a scar. The most extreme example of this is a ventricular aneurysm where all of the muscle fibers in the area are destroyed and replaced by fibrous scar tissue.

Even if the ventricular dysfunction as a result of the infarct is not immediately life-threatening, a common sequela of a transmural myocardial infarction in the left ventricle is heart failure brought about by ventricular remodeling. Left ventricular remodeling is a physiological process in response to the hemodynamic effects of the infarct that causes changes in the shape and size of the left ventricle. Remodeling is initiated in response to a redistribution of cardiac stress and strain caused by the impairment of contractile function in the infarcted area as well as in nearby and/or interspersed viable myocardial tissue with lessened contractility due to the infarct. The remodeling process following a transmural infarction starts with an acute phase which lasts only for a few hours. The infarcted area at this stage includes tissue undergoing ischemic necrosis and is surrounded by normal myocardium. Over the next few days and months after scar tissue has formed, global remodeling and chamber enlargement occur in a third phase due to complex alterations in the architecture of the left ventricle involving both infarcted and non-infarcted areas. Remodeling is thought to be the result of a complex interplay of hemodynamic, neural, and hormonal factors.

It has been shown that the extent of ventricular remodeling is positively correlated with increased mortality in post-MI patients. It is with reversing and/or preventing such ventricular remodeling that the present invention is primarily concerned.

SUMMARY

The part of the myocardium that is most vulnerable to the post-infarct remodeling process is the infarct region, which is an area that includes sites in and around the infarct where the myocardial fibers are still intact but contractile function is impaired. The infarct region is thus the area most likely to undergo progressive dilation described above with wall thinning and further impairment of function. By pacing myocardial sites in proximity to the infarct with appropriately timed pacing pulses, the infarct region is pre-excited in a manner that lessens the mechanical stress to which it is subjected, thus reducing the stimulus for remodeling. Pre-excitation of one or more myocardial sites for the purpose of controlling remodeling, however, may have an adverse effect on cardiac function by causing less efficient pumping. It would be desirable to track cardiac function in order to provide a feedback mechanism for delivering such remodeling control pacing in a manner which does not unduly compromise a patient's hemodynamics. In other situations, pre-excitation pacing may have a positive effect on cardiac function by shifting the mechanical load from dysfunctional regions of the myocardium to more strongly contracting regions. Described herein is a device and method for providing pre-excitation of myocardial sites to control remodeling that incorporates one or more sensing modalities for assessing cardiac function. In one embodiment, the cardiac function assessment is derived from hemodynamic pressure measurements, as well as possibly other measured parameters reflective of cardiac function. The cardiac function assessment may then be used as part of a feedback loop for controlling the delivery of remodeling control pacing. The feedback loop can also be used to control the delivery of other types of anti-remodeling therapy such as neuromodulation.

DETAILED DESCRIPTION

Figure 1:
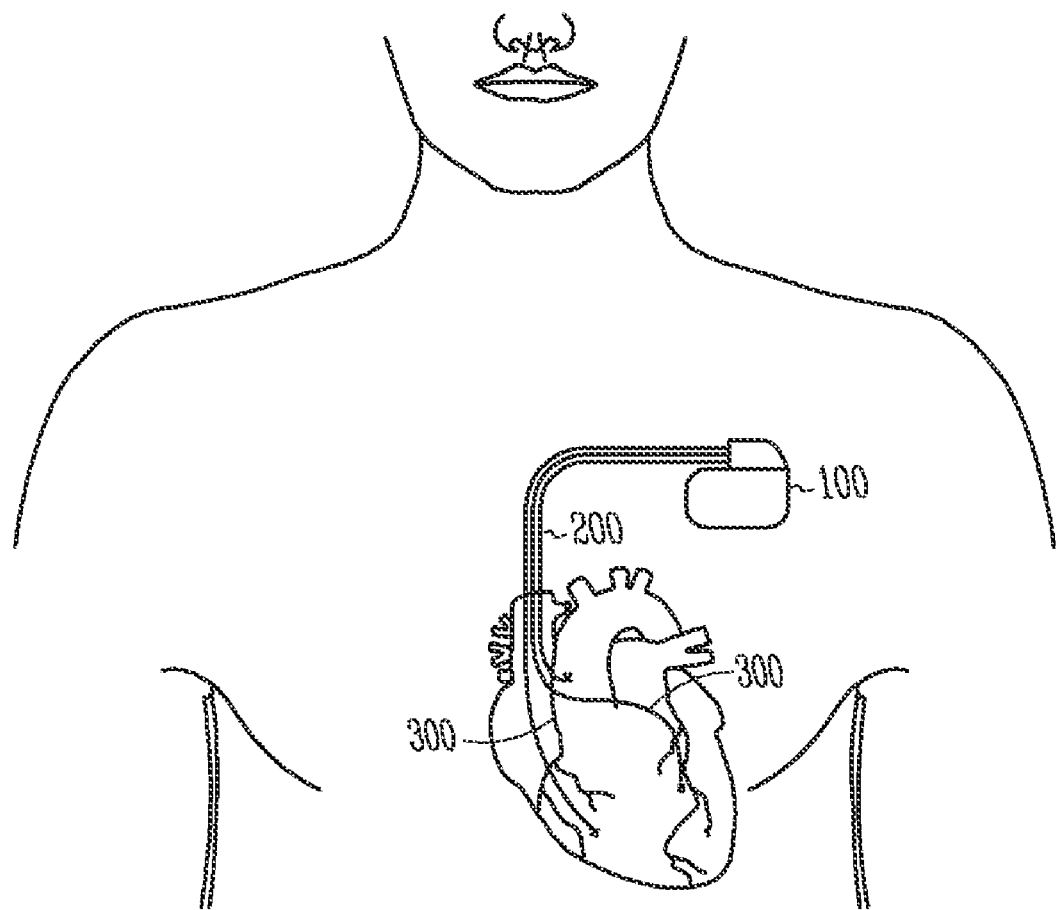
FIG. 1 illustrates the physical placement of an implantable cardiac device.

The degree to which a heart muscle fiber is stretched before it contracts is termed the preload, while the degree of tension or stress on a heart muscle fiber as it contracts is termed the afterload. The maximum tension and velocity of shortening of a muscle fiber increases with increasing preload, and the increase in contractile response of the heart with increasing preload is known as the Frank-Starling principle. When a myocardial region contracts late relative to other regions, the contraction of those other regions stretches the later contracting region and increases its preloading, thus causing an increase in the contractile force generated by the region. Conversely, a myocardial region that contracts earlier relative to other regions experiences decreased preloading and generates less contractile force. Because pressure within the ventricles rises rapidly from a diastolic to a systolic value as blood is pumped out into the aorta and pulmonary arteries, the parts of the ventricles that contract earlier during systole do so against a lower afterload than do parts of the ventricles contracting later. Thus, if a ventricular region can be made to contract earlier than parts of the ventricle, it will be subjected to both a decreased preload and afterload which decreases the mechanical stress experienced by the region relative to other regions during systolic contraction. The region will also do less work thus lessening its metabolic demands and the degree of any ischemia that may be present.

If the region around an infarct were made to contract during early systole, it would be subjected to less distending forces and less likely to undergo expansion, especially during the period immediately after a myocardial infarction. In order to cause early contraction and lessened stress, electro-stimulatory pacing pulses may be delivered to one or more sites in or around the infarct in a manner that pre-excites those sites relative to the rest of the ventricle. (As the term is used herein, a pacing pulse is any electrical stimulation of the heart of sufficient energy to initiate a propagating depolarization, whether or not intended to enforce a particular heart rate.) In a normal heartbeat, the specialized His-Purkinje conduction network of the heart rapidly conducts excitatory impulses from the sino-atrial node to the atrio-ventricular node, and thence to the ventricular myocardium to result in a coordinated contraction of both ventricles. Artificial pacing with an electrode fixed into an area of the myocardium does not take advantage of the heart's normal specialized conduction system for conducting excitation throughout the ventricles because the specialized conduction system can only be entered by impulses emanating from the atrio-ventricular node. Thus the spread of excitation from a ventricular pacing site must proceed only via the much slower conducting ventricular muscle fibers, resulting in the part of the ventricular myocardium stimulated by the pacing electrode contracting well before parts of the ventricle located more distally to the electrode. This pre-excitation of a paced site relative to other sites can be used to deliberately change the distribution of wall stress experienced by the ventricle during the cardiac pumping cycle in order to prevent or reduce the remodeling that would otherwise occur. This deliberate change in the distribution of wall stress by pre-excitation pacing will mechanically unload the overstressed region of the ventricular myocardium. Pre-excitation of the infarct region relative to other regions unloads the infarct region from mechanical stress by decreasing its afterload and preload, thus preventing or minimizing the remodeling that would otherwise occur. Pacing therapy to unload the infarct region may be implemented by pacing the ventricles at a single site in proximity to the infarct region or by pacing at multiple ventricular sites in such proximity. In the latter case, the pacing pulses may be delivered to the multiple sites simultaneously or in a defined pulse output sequence. As described below, the single-site or multiple site pacing may be performed in accordance with a bradycardia pacing algorithm such as an inhibited demand mode or a triggered mode.

Another way of controlling ventricular remodeling is by delivering electrostimulation to autonomic nerves. As the heart begins to compensatorily dilate following an MI, afferent baroreceptor and cardiopulmonary receptor signals are sent to the vasomotor central nervous system control center, which responds with hormonal secretion and sympathetic discharge. It is the combination of hemodynamic, sympathetic nervous system and hormonal alterations (such as presence or absence of angiotensin converting enzyme (ACE) activity) that ultimately account for the deleterious alterations in cell structure involved in ventricular remodeling. The sustained stresses causing hypertrophy induce apoptosis (i.e., programmed cell death) of cardiac muscle cells and eventual wall thinning which causes further deterioration in cardiac function. The activity of the autonomic nervous system is thus at least partly responsible for the ventricular remodeling which occurs as a consequence of an MI or due to heart failure. It has been demonstrated that remodeling can be affected by pharmacological intervention with the use of, for example, ACE inhibitors and beta-blockers. Pharmacological treatment carries with it the risk of side effects, however, and it is also difficult to modulate the effects of drugs in a precise manner. Electrostimulatory means may be employed to modulate autonomic activity, referred to as neurostimulation therapy, for the purpose of controlling ventricular remodeling by either stimulating parasympathetic activity or inhibiting sympathetic activity. Such neurostimulation therapy may be delivered alone or in conjunction with remodeling control pacing as described above.

Pre-excitation of a particular myocardial site or sites in order to lessen the mechanical stress to which they are subjected during systole may also, however, have the unfortunate effect of compromising cardiac function. This can come about because pre-excitation of a ventricular region causes that region to contract earlier than other regions, resulting in an asynchronous contraction of the ventricle. Such an asynchronous contraction may be less efficient than in the normal situation where all regions of the ventricle contract almost simultaneously. Pre-excitation may also cause a decrease in preload and/or filling time of the left ventricle resulting in a decreased volume of blood in the left ventricle at systole. Post-MI patients with already weakened hearts may not tolerate these effects well and may exhibit lessened systolic pressure and/or stroke volume. Described herein is a device and method which provides pre-excitation of myocardial sites to control remodeling and which also monitors cardiac function in order to deliver stress reducing pre-excitation pacing (as well as neurostimulation in certain embodiments) in a feedback-controlled manner which does not unduly compromise a patient's hemodynamics. Feedback control of pre-excitation pacing may also be used to deliver such pacing in an optimal manner in situations where it has a positive effect on cardiac function.

1. Exemplary Device Description

As shown in FIG. 1, an implantable cardiac device 100 for delivering CRT is typically placed subcutaneously or submuscularly in a patient's chest with leads 200 threaded intravenously into the heart to connect the device to electrodes 300 used for sensing and pacing of the atria and/or ventricles. Electrodes may also be positioned on the epicardium by various means. A programmable electronic controller causes the pacing pulses to be output in response to lapsed time intervals and sensed electrical activity (i.e., intrinsic heart beats not as a result of a pacing pulse). The device senses intrinsic cardiac electrical activity through a sensing channel which incorporates internal electrodes disposed near the chamber to be sensed. A depolarization wave associated with an intrinsic contraction of the atria or ventricles that is detected by the device is referred to as an atrial sense or ventricular sense, respectively. In order to cause such a contraction in the absence of an intrinsic beat, a pacing pulse with energy above a certain threshold is delivered to the chamber through a pacing channel which incorporates internal electrodes disposed near the chamber to be paced.

In an exemplary embodiment, an implantable device for delivering cardiac therapy to post-MI patients includes one or more pacing channels for delivering pacing pulses to one or more ventricular sites. The controller is programmed to deliver pacing which pre-excites a region of the ventricular myocardium so as to mechanically unload that region during systole. The therapy may be delivered as single-site pacing, biventricular pacing where one of the ventricles is pre-excited relative to the other as determined by a programmed biventricular offset interval, or delivered as multi-site ventricular pacing where at least one of the ventricles is paced at a plurality of sites so as to pre-excite one or more of the sites relative to the other sites. In any case, the ventricular pacing may be delivered in a non-atrial tracking mode where a ventricular escape interval is defined between ventricular paces, or in an atrial tracking mode where the ventricular paces are delivered after a defined atrio-ventricular escape interval following an atrial sense. In a patient who is chronotropically incompetent, an atrial pacing channel may also be provided for pacing the atria, with the ventricular pace(s) delivered upon expiration of the atrio-ventricular escape interval following the atrial pace.

A block diagram of an exemplary implantable device for delivering pre-excitation pacing therapy to a site or sites in proximity to an infarct as described above is illustrated in FIG. 2. Pacemakers are usually implanted subcutaneously in the patient's chest and connected to sensing/pacing electrodes by leads either threaded through the vessels of the upper venous system to the heart or by leads that penetrate the chest wall. (As the term is used herein, a "pacemaker" should be taken to mean any cardiac rhythm management device with a pacing functionality regardless of any other functions it may perform.) The controller of the pacemaker is made up of a microprocessor 10 communicating with a memory 12 via a bidirectional data bus, where the memory 12 typically comprises a ROM (read-only memory) and a RAM (random-access memory) for program or data storage. The controller could be implemented by other types of logic circuitry (e.g., discrete components or programmable logic arrays) using a state machine type of design, but a microprocessor-based system is preferable. The controller is capable of operating the pacemaker according to one or more a predetermined algorithms. In one example, the algorithms used are traditional pacemaker pacing modes where such a programmed pacing mode defines how pacing pulses are output in response to sensed events and expiration of time intervals. A telemetry unit 80 is also provided for communicating with an external programmer or other monitoring device. An external programmer is basically a computer with an input means allowing a user to program the implantable device and a display means for presenting data communicated to it by the implantable device.

Figure 2:
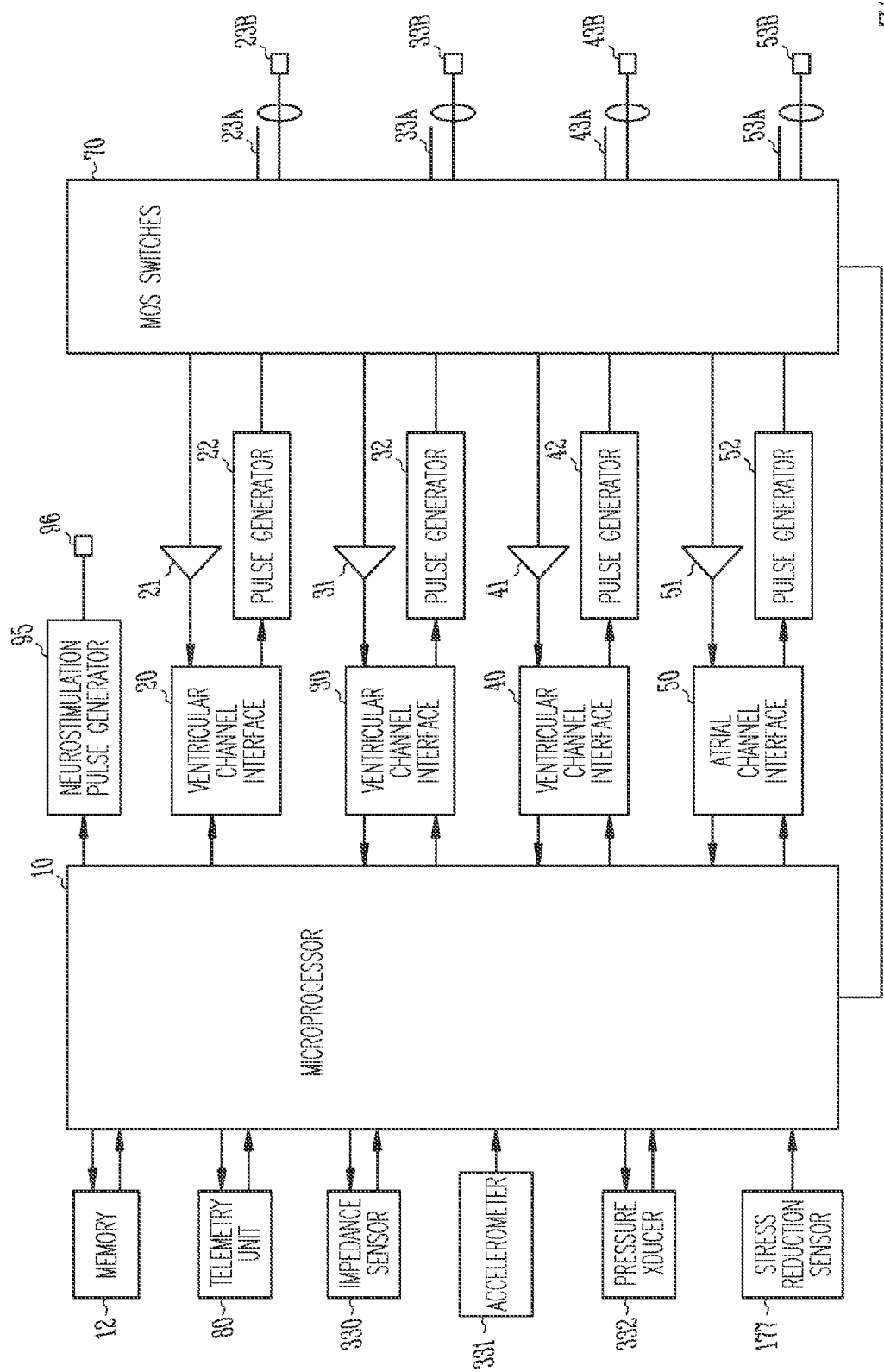
FIG. 2 is a system diagram of a cardiac device configured for multi-site stimulation and sensing.

The device illustrated in FIG. 2 has multiple sensing and pacing channels and is therefore capable of delivering single-site or multiple site ventricular pacing. The multiple sensing and pacing channels may be configured as either atrial or ventricular channels allowing the device to deliver such pacing with or without atrial tracking. Shown in FIG. 2 is a configuration with one atrial sensing/pacing channel and three ventricular sensing/pacing channels. The atrial sensing/pacing channel comprises ring electrode 53a, tip electrode 53b, sense amplifier 51, pulse generator 52, and an atrial channel interface 50 which communicates bidirectionally with a port of microprocessor 10. The three ventricular sensing/pacing channels that include ring electrodes 23a, 33a, and 43a, tip electrodes 23b, 33b, and 43b, sense amplifiers 21, 31, and 41, pulse generators 22, 32, and 42, and ventricular channel interfaces 20, 30, and 40. A pacing channel is made up of the pulse generator connected to the electrode while a sensing channel is made up of the sense amplifier connected to the electrode. The channel interfaces include analog-to-digital converters for digitizing sensing signal inputs from the sensing amplifiers, registers that can be written to for adjusting the gain and threshold values of the sensing amplifiers, and registers for controlling the output of pacing pulses and/or changing the pacing pulse parameters (e.g., pulse width and amplitude). In certain patients, pacing of sites in proximity to an infarct or within ischemic regions may be less excitable than normal and require an increased pacing energy in order to achieve capture (i.e., initiating of a propagating action potential). For each channel, the same electrode pair can be used for both sensing and pacing. In this embodiment, bipolar leads that include two electrodes are used for outputting a pacing pulse and/or sensing intrinsic activity. Other embodiments may employ a single electrode lead for sensing and pacing in each channel, known as a unipolar lead. When a single electrode on a lead is used for pacing or sensing, the second electrode necessary for pacing or sensing can be provided by the case of implantable cardiac device 100 or by an electrode on another lead. A MOS switching network 70 controlled by the microprocessor is used to switch the electrodes from the input of a sense amplifier to the output of a pulse generator as well as configure sensing or pacing channels with the available electrodes. The switching network 70 may also be used to vary which of the available electrodes are used to deliver pre-excitation pacing, referred to as the pacing configuration.

The controller controls the overall operation of the device in accordance with programmed instructions stored in memory. The controller interprets electrogram signals from the sensing channels and controls the delivery of paces in accordance with a pacing mode. The sensing circuitry of the pacemaker generates atrial and ventricular electrogram signals from the voltages sensed by the electrodes of a particular channel. When an electrogram signal in an atrial or sensing channel exceeds a specified threshold, the controller detects an atrial or ventricular sense, respectively, which pacing algorithms may employ to trigger or inhibit pacing.

Pre-excitation therapy is most conveniently delivered in conjunction with a bradycardia pacing mode. Bradycardia pacing modes refer to pacing algorithms used to pace the atria and/or ventricles in a manner that enforces a certain minimum heart rate. For example, a ventricular escape interval for pacing the ventricles can be defined between ventricular events, referred to as the cardiac cycle (CC) interval with its inverse being the lower rate limit or LRL. The CC interval is restarted with each ventricular sense or pace. In atrial tracking and AV sequential pacing modes, another ventricular escape interval is defined between atrial and ventricular events, referred to as the AV delay (AVD) interval, where a ventricular pacing pulse is delivered upon expiration of the AV delay interval if no ventricular sense occurs before expiration of the AV delay interval. In an atrial tracking mode, the atrio-ventricular pacing delay interval is triggered by an atrial sense and stopped by a ventricular sense or pace. An atrial escape interval can also be defined for pacing the atria either alone or in addition to pacing the ventricles. In an AV sequential pacing mode, the atrio-ventricular delay interval is triggered by an atrial pace and stopped by a ventricular sense or pace. Atrial tracking and AV sequential pacing are commonly combined so that an AVD interval starts with either an atrial pace or sense.

In the case where the pre-excitation pacing of the ventricle is delivered at multiple sites, the sites may be paced simultaneously or in accordance with a particular pulse output sequence that specifies the order in which the sites are to be paced during a single beat. For example, pre-excitation pacing may involve biventricular pacing with the paces to right and left ventricles delivered either simultaneously or sequentially, with the interval between the paces termed the offset interval (also sometimes referred to as the VV delay or VV offset interval). The offset interval may be zero in order to pace both ventricles simultaneously or non-zero in order to pace the left and right ventricles sequentially. As the term is used herein, a negative offset refers to pacing the left ventricle before the right, while a positive offset refers to pacing the right ventricle first. In the case of multi-site pre-excitation pacing of a ventricle, separate VV offset intervals with respect to, e.g., a right ventricular pace may be specified for each paced site. A common way of implementing multi-site ventricular pacing, biventricular pacing, or left ventricle-only pacing is to base the timing upon only right ventricular activity so that ventricular escape intervals are reset or stopped by right ventricular senses.

As the term is used herein for left ventricle-only pacing, biventricular pacing, or multi-site ventricular pacing, the AVD interval refers to the interval between an atrial event (i.e., a pace or sense in one of the atria, usually the right atrium) and the first ventricular pace which pre-excites one of the ventricles. For example, in the case of biventricular pacing, the pacing instant for the non-pre-excited ventricle is specified by the VV interval so that it is paced at an interval AVD+VV after the atrial event. The AVD interval may be the same or different depending upon whether it is initiated by an atrial sense or pace (i.e., in atrial tracking and AV sequential pacing modes, respectively).

The device may also incorporate a neurostimulation channel which includes a neurostimulation pulse generator 95 and an electrode 96. The controller may then be further programmed to deliver neurostimulation therapy for the purpose of controlling ventricular remodeling by inhibiting sympathetic nerve activity or by stimulating parasympathetic activity. For sympathetic inhibition, a lead incorporating the electrode 96 may be adapted for disposition near an arterial baroreceptor or afferent nerve of a baroreflex arc. Stimulation of the baroreflex arc then results in inhibition of sympathetic activity. The electrode 96 may be intravascularly positioned in a blood vessel or elsewhere proximate to a baroreceptor or afferent nerve such as in a pulmonary artery or a cardiac fat pad. For parasympathetic stimulation, a lead incorporating the electrode 96 is adapted for disposition near a parasympathetic nerve. The electrode 96 in this case may be a nerve cuff electrode adapted for disposition around a parasympathetic nerve (e.g., the vagus nerve) or an intravascular electrode for transvascularly stimulating a parasympathetic nerve adjacent to a blood vessel.

2. Assessment of Cardiac Function

In order to maintain optimum hemodynamics during pre-excitation pacing, the delivery of such pacing may be modulated in accordance with an assessment of cardiac function. Such an assessment of cardiac function may be derived from measurements of one or more cardiac function parameters. One or more additional sensing modalities may be incorporated into the implantable device for this purpose, where the additional sensors are interfaced to the microprocessor 10. The measurements of cardiac function parameters may constitute averages of individual measurements taken over some specified period of time. A cardiac function assessment may simply be a cardiac function parameter or a may be a function of one or more such parameters. The cardiac function assessment is compared with specified threshold values or ranges of values in order to determine if the patient's cardiac function is at an acceptable level. The delivery of pre-excitation pacing can then be modulated in accordance with that determination.

Hemodynamic pressure measurements are examples of cardiac function parameters which directly reflect cardiac function. The implantable device shown in FIG. 2 is equipped with a pressure sensor 332. The pressure sensor 332 may be placed in or near an element of the cardiovascular system that allows measurement of hemodynamic pressure. Elements of the cardiovascular system include veins, arteries, cardiac chambers, and other items that assist in the distribution of blood within the body. The pressure sensor 332 may be attached to an intravascular lead and be appropriately disposed for measuring diastolic filling pressures and/or systolic pulse pressures. (Other embodiments may employ in implanted pressure sensor which communicates with the implantable device by an RF or ultrasonic link instead of a lead.) The pressure sensor 332 may be placed, for example, either in the pulmonary artery, left atrium, or left ventricle. Based on the pressure signal, the device may be programmed to calculate maximum, minimum, and mean pressures as well as maximum/minimum derivatives of the pressure with respect to time. The pressure measurements may also be modified based on physiologic conditions such as the patient's activity level, posture, heart rate, and respiratory rate or upon environmental conditions such as atmospheric pressure or the patient's altitude. A multi-axis accelerometer 331 may be used in order to determine the patient's posture. The modification of the pressure measurements based on physiologic or environmental conditions may include, for example, modifying the measurement to compensate for the condition, initiation of pressure measurements, termination of pressure measurements, and/or changing the sensitivity of the pressure sensor.

Another cardiac function parameter is cardiac output, which may be measured by an impedance technique in which transthoracic impedance is measured and used to compute stroke volume. An impedance sensor 330 includes an exciter and an impedance measuring circuit. Processing of the impedance signal allows the derivation of a signal representing respiratory activity and/or cardiac blood volume, depending upon the location the voltage sense electrodes in the thorax. (See, e.g., U.S. Pat. Nos. 5,190,035 and 6,161,042, assigned to the assignee of the present invention and hereby incorporated by reference.) If the electrodes are located so as to measure impedance across the lungs, the patient's minute ventilation may be derived from the respiratory activity signal and may be used as an indication of exertion level. If the electrodes are located to measure impedance across the heart, the impedance signal is filtered to remove the respiratory component, the result is a signal that is representative of blood volume in the heart at any point in time, thus allowing the computation of stroke volume and, when combined with heart rate, computation of cardiac output. The stroke volume integrated over time (or averaged and multiplied by heart rate) gives the patient's cardiac output.

Cardiac function may be further assessed by measuring cardiac output and/or cardiovascular pressure and comparing it a threshold value or range which may be a function of the patient's measured exertion level, where exertion level may be measured by an impedance sensor configured to measure minute ventilation as described above, by an accelerometer 331 for measuring physical activity level, or by heart rate if the patient is chronotropically competent. A look-up table or other function may be used to compute what cardiac output or cardiovascular pressure is considered adequate for a given exertion level.

Other possible cardiac function parameters that may be derived by the device from impedance measurements include ventricular volumes at various stages of the cardiac cycle such as end-diastolic volumes, end-systolic volumes, and ejection fraction. The device may also measure delays between electrical events (as determined from electrograms) and pressure signals and/or delays between cardiac motion (as determined by measuring trans-cardiac impedance) signals and pressure signals.

3. Feedback Control of Pre-Excitation Pacing

A cardiac assessment derived from one or more cardiac function parameters as described above may be employed to modulate the delivery of pre-excitation pacing for reducing remodeling in post-MI patients in a feedback-controlled manner. The modulation of pre-excitation pacing may include starting or stopping pre-excitation pacing, adjustment of the AV delay used to deliver the ventricular paces in atrial tracking or AV sequential pacing modes, adjustment of offset intervals, adjustment of the pacing rate, or changes in the pacing sites used to deliver the pre-excitation pacing by switching among available pacing electrodes. As has been noted, pre-excitation pacing delivered to de-stress selected myocardial regions can have an adverse effect on cardiac function, but may also have a positive effect in certain situations. In some cases, the effect of such pre-excitation pacing in a patient may be ascertained by clinical testing. That information may then be programmed into the implantable device so that its feedback control of pre-excitation pacing will respond appropriately to changes in the cardiac function assessment. In other cases, it may not be clear how the patient's cardiac function will be changed by pre-excitation pacing. For example, the patient's cardiac function may be affected differently depending upon the setting of certain pre-excitation parameters (e.g., offset interval or AV delay) or upon which pacing sites are being used. Also, the way a patient's cardiac function reacts to pre-excitation pacing may change over time. In one embodiment, the device may be programmed to trend cardiac function parameters over time in relation to pre-excitation parameters. For example, the device may trend pressure measurements and other diagnostic measurements (e.g. heart rate, respiratory rate, impedance-based stoke volume) simultaneously with one or more therapy settings (e.g. AV delay, offset interval, or pacing sites). The computed trend in cardiac function versus the therapy settings may then be employed by the device to appropriately adjust the pre-excitation pacing when the patient's cardiac function assessment drops below a specified threshold level.

The amount of pre-excitation pacing delivered by the device can be controlled in different ways, such as by starting and stopping the pre-excitation pacing, adjusting the duration for which pre-excitation pacing is applied, varying the particular sites to which paces are delivered, adjusting the pacing rate, or by adjusting pre-excitation parameters. Examples of pre-excitation parameters are the AV delay or AVD used for pre-excitation pacing in atrial tracking or AV sequential pacing modes and the VV offset. Delivering electrical pacing therapy near an infarct region reduces wall stress in that region to the extent that the region contracts before other regions contract due to intrinsic activation, and that the effect is dependent on the AV delay and the VV offset. As the AV delay shortens and/or the VV offset is increased, the pre-excited sites are paced sooner, and the absolute amount of unloading in the region (as measured by a decrease in regional stroke work) is increased. The amount of pre-excitation also varies with the pacing configuration (i.e., the number and placement of pre-excitation pacing sites) which determines of the size of the unloaded region.

Figure 3:
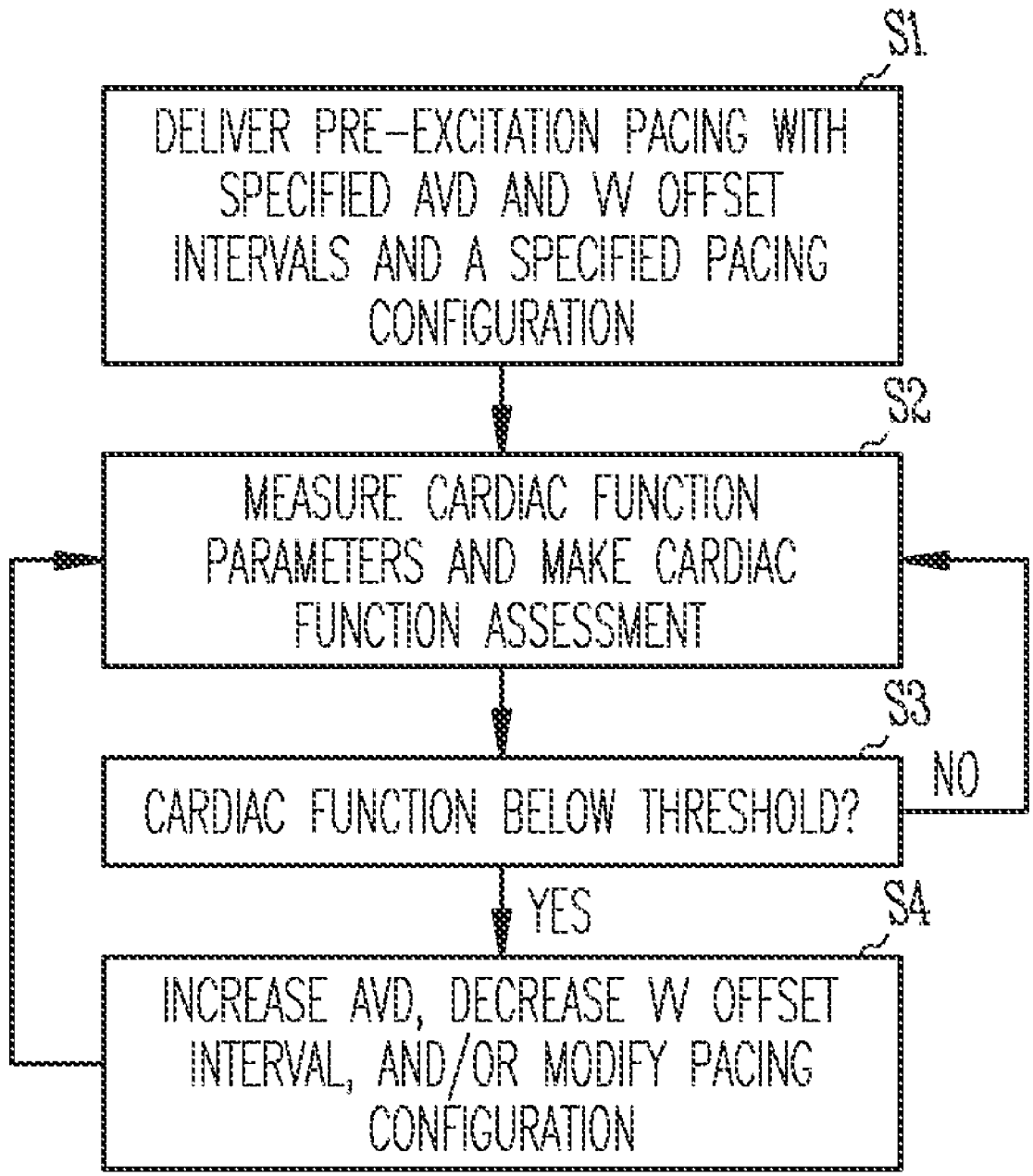
FIG. 3 illustrates an exemplary algorithm for modulating pre-excitation pacing.

Most commonly, as the amount of pre-excitation is increased, cardiac function is reduced due to ventricular asynchrony and/or sub-optimal diastolic filling of the ventricles. In order to provide a balance between the amount of unloading and the compromise of cardiac function, the device may be programmed to provide a closed-loop system for ensuring that cardiac function is not overly compromised. FIG. 3 illustrates an exemplary algorithm executable by the device that decreases the amount of pre-excitation pacing if a cardiac function assessment indicates that patient's cardiac function has decreased below a specified threshold level. At step S1, the device is initially programmed to deliver pre-excitation pacing with specified AVD and VV offset intervals and with a specified pacing configuration. At step S2, the device monitors cardiac function using one or more of the techniques described above. In one embodiment, the cardiac function assessment constitutes measurements from a pressure sensor. The types of pressure measurements used for feedback control may include, for example, minimum, mean, median and/or maximum values of instantaneous pressure, pressure averages over a predetermined interval (e.g. 1 cycle, 1 minute), pulse pressure, differential pressure, and time derivatives of pressure. As described above, the device could also use measurements of other parameters (e.g. heart rate, stroke volume) in conjunction with pressure to form the cardiac assessment. Also, the pressure measurements acquired during a first condition (e.g. when the patient is inactive) may be used differently than pressure measurements acquired during a second condition (e.g. when the patient's activity level is high). At step S3, the cardiac function assessment is compared with a threshold value or range to determine if the patient's cardiac function is at an acceptable level. If cardiac function is adequate, the device continues to monitor cardiac function while delivering pre-excitation pacing at step S2. If cardiac function is found to be inadequate, the amount of pre-excitation pacing is modified at step S4 by increasing the AV delay, decreasing the VV offset, and/or changing the pacing configuration. In other embodiments, the device may be programmed with multiple thresholds or ranges to which the cardiac function assessment is compared at step S3. The particular modification made to the pre-excitation pacing at step S4 may then depend upon the level of the patient's cardiac function. The device may also maintain a history of the patient's cardiac function and prior modifications made to the pre-excitation pacing. Depending upon the cardiac function assessment and the history, the device may then modify the pre-excitation pacing to either increase or decrease the amount of pre-excitation therapy by, for example, increasing or decreasing the AV delay or VV offset, initiating or terminating pre-excitation pacing therapy, or changing the pacing configuration. In an embodiment where the device is configured to deliver neurostimulation therapy, parameters affecting the level of such neurostimulation (e.g., initiation, termination, pulse rate, and pulse energy) may also be modified in accordance with the cardiac function assessment.

Figure 4:
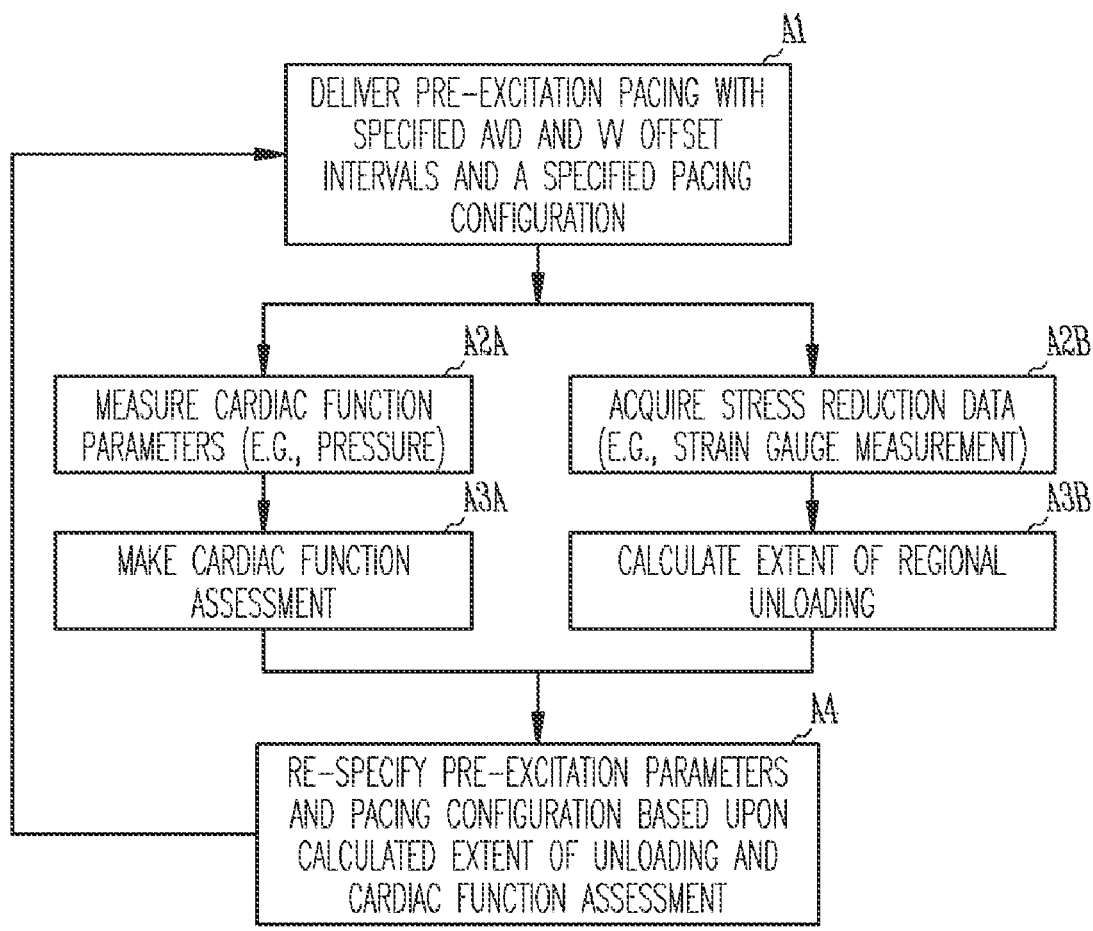
FIG. 4 illustrates an additional exemplary algorithm for modulating pre-excitation pacing.

In another embodiment, the device is configured to monitor both cardiac function and the level of stress reduction provided by the pre-excitation pacing. The extent of regional mechanical unloading (i.e., stress reduction) brought about by the pre-excitation pacing can be computed from one or more stress reduction parameters as measured by a stress reduction sensor 177 which may be, for example, an ultrasonic transducer connected to an intravascular lead for measuring wall thickness, an impedance sensor for determining mechanical activation time, and/or a local strain gauge connected to a cardiac lead (or implanted separately) for measuring regional stress. The device may then be programmed to automatically adjust one or more pre-excitation parameters based upon the cardiac function assessment and the extent of regional mechanical unloading. For example, the device may be programmed to maintain a specified ratio between the extent of unloading and the level of cardiac function. FIG. 4 illustrates an exemplary algorithm. At step A1, the device delivers pre-excitation pacing with specified AVD and VV offset intervals and a specified pacing configuration. The device periodically then measures cardiac function parameters (e.g., pressure) and computes a cardiac function assessment at steps A2a and A3a, respectively. Concomitantly, the device acquires stress reduction data (e.g., strain gauge measurement) and calculates the extent of regional unloading at steps A2b and A3b, respectively. At step A4, the device respecifies the pre-excitation parameters and pacing configuration based upon calculated extent of unloading and cardiac function assessment and then returns to step A1.

Although the invention has been described in conjunction with the foregoing specific embodiments, many alternatives, variations, and modifications will be apparent to those of ordinary skill in the art. Such alternatives, variations, and modifications are intended to fall within the scope of the following appended claims.

What is claimed is:

1. An implantable device for delivering cardiac therapy to a patient, comprising:
   one or more pulse generators for delivering pacing pulses to one or more ventricular sites;
   a controller for controlling the delivery of pacing pulses to one or more ventricular sites during a cardiac cycle in accordance with a programmed pacing algorithm;
   wherein the controller is programmed to deliver pre-excitation pacing which pre-excites a region of the ventricular myocardium so as to mechanically unload a region of the ventricular myocardium during systole;
   a pressure sensor for acquiring a cardiovascular pressure measurement; and,
   wherein the controller is programmed to compute a cardiac function assessment based upon the pressure measurement, monitor cardiac function while delivering pre-excitation pacing by comparing the cardiac function assessment to a specified threshold, and, if the cardiac function assessment is less than the specified threshold to indicate worsened cardiac function, decrease the amount of pre-excitation pacing delivered.

2. The device of claim 1 wherein the controller is programmed to decrease the amount of pre-excitation pacing by adjusting an AV delay used to deliver the pre-excitation pacing in an atrial tracking or AV sequential pacing mode.

3. The device of claim 1 wherein the controller is programmed to decrease the amount of pre-excitation pacing by adjusting a VV offset delay used to deliver the pre-excitation pacing to two or more ventricular sites.

4. The device of claim 1 wherein the controller is programmed to decrease the amount of pre-excitation pacing by adjusting a pacing configuration used to deliver the pre-excitation pacing.

5. The device of claim 1 wherein the controller is programmed to decrease the amount of pre-excitation pacing by stopping the delivery of pre-excitation pacing.

6. The device of claim 1 wherein the controller is further programmed to derive a cardiac function assessment from the pressure measurement and one or more other measured cardiac function parameters and adjust the amount of pre-excitation pacing based upon the cardiac function assessment.

7. The device of claim 6 further comprising:
   an exertion level sensor; and,
   wherein the controller is programmed to derive the cardiac function assessment based upon the pressure measurement and the measured exertion level.

8. The device of claim 1 wherein the controller is programmed to trend pressure measurements in relation to the amount of pre-excitation pacing delivered in order to determine the effect of the pre-excitation pacing on cardiac function.

9. The device of claim 1 further comprising:
   an stress reduction sensor; and,
   wherein the controller is programmed to derive the extent of regional unloading based upon the stress reduction sensor data and to adjust the amount of pre-excitation pacing based upon the extent of regional unloading and the cardiac function assessment.

10. A method for delivering cardiac therapy to a patient, comprising:
    delivering pre-excitation pacing pulses via an implantable cardiac device to one or more ventricular sites in a manner which pre-excites a region of the ventricular myocardium so as to mechanically unload a region of the ventricular myocardium during systole;
    configuring the implantable cardiac device to acquire a cardiovascular pressure measurement; and,
    configuring the implantable cardiac device to compute a cardiac function assessment based upon the pressure measurement, monitor cardiac function while delivering pre-excitation pacing by comparing the cardiac function assessment to a specified threshold, and, if the cardiac function assessment is less than the specified threshold to indicate worsened cardiac function, decrease the amount of pre-excitation pacing delivered.

11. The method of claim 10 further comprising configuring the implantable cardiac device to decrease the amount of pre-excitation pacing by adjusting an AV delay used to deliver the pre-excitation pacing in an atrial tracking or AV sequential pacing mode.

12. The method of claim 10 further comprising configuring the implantable cardiac device to decrease the amount of pre-excitation pacing by adjusting a VV offset delay used to deliver the pre-excitation pacing to two or more ventricular sites.

13. The method of claim 10 further comprising configuring the implantable cardiac device to decrease the amount of pre-excitation pacing by adjusting a pacing configuration used to deliver the pre-excitation pacing.

14. The method of claim 10 further comprising configuring the implantable cardiac device to decrease the amount of pre-excitation pacing by stopping the delivery of pre-excitation pacing.

15. The method of claim 10 further comprising configuring the implantable cardiac device to derive a cardiac function assessment from the pressure measurement and one or more other measured cardiac function parameters and adjusting the amount of pre-excitation pacing based upon the cardiac function assessment.

16. The method of claim 15 further comprising configuring the implantable cardiac device to:
    measure an exertion level; and,
    derive the cardiac function assessment based upon the pressure measurement and the measured exertion level.

17. The method of claim 10 further comprising configuring the implantable cardiac device to trend pressure measurements in relation to the amount of pre-excitation pacing delivered in order to determine the effect of the pre-excitation pacing on cardiac function.

18. The method of claim 10 further comprising configuring the implantable cardiac device to:
    acquire stress reduction data; and,
    derive the extent of regional unloading based upon the stress reduction data and adjusting the amount of pre-excitation pacing based upon the extent of regional unloading and the cardiac function assessment.

* * * * *